United States Patent [19]
Wild et al.

[11] Patent Number: 5,281,536
[45] Date of Patent: Jan. 25, 1994

[54] STABLE LIQUID CONTROL SERUM OR CALIBRATION SYSTEM FOR USE IN CLINICAL DIAGNOSTICS

[75] Inventors: Thomas Wild, Weilheim; Peter Stegmueller, Augsburg, both of Fed. Rep. of Germany

[73] Assignee: Boehringer Mannheim GmbH, Mannheim, Fed. Rep. of Germany

[21] Appl. No.: 964,755

[22] Filed: Oct. 22, 1992

[30] Foreign Application Priority Data

Oct. 26, 1991 [DE] Fed. Rep. of Germany ....... 4135404

[51] Int. Cl.$^5$ ............................................. G01N 31/00
[52] U.S. Cl. ............................................ 436/16; 436/8; 436/12; 436/97; 436/176; 252/408.1
[58] Field of Search ...................... 436/8–19, 436/97, 176; 252/408.1

[56] References Cited

U.S. PATENT DOCUMENTS

| | | | |
|---|---|---|---|
| 3,876,375 | 4/1975 | Maurukas | 436/16 |
| 3,973,913 | 8/1976 | Louderback | 436/18 X |
| 4,121,905 | 10/1978 | Maurukas | 436/12 X |
| 4,201,694 | 5/1980 | Louderback | 436/12 |
| 4,288,343 | 9/1981 | Louderback | 436/12 |
| 4,299,726 | 11/1981 | Crews et al. | 436/16 X |
| 4,344,864 | 8/1982 | Louderback et al. | 436/12 |
| 4,438,202 | 3/1984 | Engler et al. | 436/8 |
| 4,643,976 | 2/1987 | Hoskins | 436/15 |

FOREIGN PATENT DOCUMENTS

| | | |
|---|---|---|
| 0082587 | 6/1983 | European Pat. Off. . |
| 0131826 | 1/1985 | European Pat. Off. . |
| 0184765 | 6/1986 | European Pat. Off. . |

OTHER PUBLICATIONS

Experientia vol. 28, 1972, pp. 379–380.

*Primary Examiner*—James C. Housel
*Assistant Examiner*—Maureen M. Wallenhorst
*Attorney, Agent, or Firm*—Felfe & Lynch

[57] ABSTRACT

A stable liquid control and/or calibration serum for use in clinical diagnostics containing a liquid-stable bilirubin derivative and a known concentration of at least one analyte. The invention further addresses a process for the preparation of the stable liquid serum.

19 Claims, No Drawings

STABLE LIQUID CONTROL SERUM OR CALIBRATION SYSTEM FOR USE IN CLINICAL DIAGNOSTICS

FIELD OF THE INVENTION

The invention concerns a stable liquid control and/or calibration serum for use in clinical diagnostics, wherein said stable liquid control and/or calibration system contains a liquid stable bilirubin derivative.

BACKGROUND AND PRIOR ART

Control and/or calibration sera or compositions referred to as control and/or calibration sera are usually used for monitoring accuracy and precision of an assay method and for the calibration of analyzers. These sera and compositions contain the parameter to be detected in known, exactly defined concentrations. A distinction is made between special control and/or calibration sera which are used to control and calibrate selected parameters or a certain limited, often related group of parameters and universal control and/or calibration sera used to control and calibrate, if possible, all conventional parameters using any of the methods that are commonly known in the practice.

In daily routine work, such products must fulfill the following requirements:
- an exactly defined concentration of the measuring parameters must be maintained
- the concentrations must be within the range of medical relevance (normal or pathological)
- handling of the control and/or calibration sera must be easy
- the control and/or calibration sera must have an extended storage stability Especially high demands are made on the handling and storage stability when these control and/or calibration sera are used on automated analyzers. To date, most control and/or calibration sera have been available as lyophilisates thus ensuring an acceptable stability until the sera are reconstituted. This method is, however, very cumbersome and requires the use of a reconstituting solution. Lyophilisates often tend to become turbid which may cause analytical errors since the results of numerous detection methods involve colorimetric evaluation. Another source of errors is incorrect pipetting of the reconstituting solution. Once reconstituted, the reference or calibration sera are stable for only a few hours at room temperature. They must, hence, be prepared fresh every day. To facilitate handling, it is therefore desirable to make avalailable a reference or calibration serum that does not require pretreatment by the operator of the analyzer.

U.S. Pat. No. 3,876,375 describes a liquid biological composition that is used as a reference serum in diagnostic analysis. 20-40% alkylene polyols having 2-5 C-atoms, such as ethylene glycol, propylene glycol, butylene glycol, pentane diol and glycerol are used to stabilize this composition. When polyols in such high concentrations are added, the control and/or calibration serum may become viscous which may lead to problems and inaccuracies during the pumping and pipetting steps of the automated analyzer. It is therefore not suitable to add alkylene polyols in high concentrations.

In the preparation of a liquid-stable control and/or calibration serum, the bilirubin substrate limits stability in most cases. The bilirubin concentration is determined when hyperbilirubinemia is diagnosed. As a lyophilisate, bilirubin is sufficiently stable whereas after reconstitution stability is reduced to only a few hours at room temperature or to appr. two weeks at −20° C.

U.S. Pat. No. 4,344,864 describes how conjugated bilirubin is stabilized by adding a sulfhydryl compound and a chelating agent at a pH of 8.2-9.2 in blood serum. For the preparation of a universal control and/or calibration serum it is, however, advantageous to use as few additives as possible. A stabilizing agent for one parameter often interferes with the determination of other parameters. Reducing agents which contain SH-groups can interfere with the subsequent enzymatic reaction, for example.

It is, hence, an object to provide a liquid control and/or calibration serum which is suitable for multiple parameter determinations in clinical diagnostics and contains bilirubin in a stabilized form. The object is accomplished by the invention which is characterized in greater detail in the disclosure which follows. The object is essentially accomplished in that the control and/or calibration serum contains a liquid-stable bilirubin derivative.

SUMMARY OF THE INVENTION

The invention hence addresses a stable liquid control and/or calibration serum containing a known concentration of at least one analyte for use in clinical diagnostics which contains a liquid-stable bilirubin derivative.

The invention further addresses a process for the preparation of a stable liquid control and/or calibration serum for use in clinical diagnostics which contains a liquid-stable bilirubin derivative on the basis of a bovine serum albumine solution. The latter solution contains the desired parameters in the desired parameter concentrations. Additives may also be added, if necessary.

The invention also adresses the use of a liquid-stable bilirubin derivative in a control and/or calibration serum. The bilirubin derivative serves to increase the storage stability of the control and/or calibration serum.

DETAILED DESCRIPTION OF PREFERRED EMBODIMENTS

The stable liquid control and/or calibration serum in accordance with the invention contains analyte parameters that are of relevance in clinical diagnostics. These parameters include bicarbonate, bilirubin, cholesterol, creatinine, iron, glucose, uric acid, urea, lactate, triglycerides, phospholipids, total protein, albumin, calcium, phosphate, magnesium, sodium, potassium, and chloride. Clinically relevant enzymes may optionally also be included.

Preferred parameter concentrations are in the clinical concentration range, i.e. those ranges where concentration values are considered normal or pathological. The concentrations of the individual parameters may, of course, vary from lot to lot within the limits indicated in table 1.

TABLE 1

Concentration ranges for the individual parameters of a liquid control and/or calibration serum.

| Substance | Concentration range [mg/dl] |
|---|---|
| bicarbonate | 268–317 |
| bilirubin | 0.25–6.00 |
| cholesterol | 125–200 |
| creatinine | 0.5–3.0 |

TABLE 1-continued

Concentration ranges for the individual parameters of a liquid control and/or calibration serum.

| Substance | Concentration range [mg/dl] |
|---|---|
| iron | 0.06–0.3 |
| glucose | 70–210 |
| uric acid | 2.5–8.5 |
| urea | 10–150 |
| lactate | 6–22 |
| triglycerides | 70–210 |
| phospholipids | 150–280 |
| total protein | 5000–9000 |
| albumin | 3500–7000 |
| calcium | 9–14 |
| phosphate | 2.5–7 |
| magnesium | 1.8–4.5 |
| sodium | 260–360 |
| potassium | 14–22.5 |
| chloride | 280–385 |

The stable liquid control and/or calibration serum of the invention does not contain free bilirubin as a parameter for the determination of bilirubin but a bilirubin derivative. When stored in a liquid form, the bilirubin derivatives of the invention surprisingly showed a significantly higher stability than non-derivatized bilirubin. The bilirubin derivatives can be prepared from free bilirubin, the soluble alkali salts thereof, e.g. sodium bilirubinate, bilirubin ester or bilirubin amides. For stabilizing the bilirubin derivatives, it is essential that an alcohol or a mercaptan, i.e. a compound containing a thiol group, be added to the vinyl group at position 18 of the tetrapyrrole ring. Thioglycolic acid, methyl thioglycolic acid, 2-mercaptoethanol or n-acetyl-L-cysteine can be added, for example. Such bilirubin derivatives are known from *Experientia* (1972). 28:379–380. The bilirubin derivatives that can be used in accordance with the invention as control and/or calibration sera are represented by the following general formula (I):

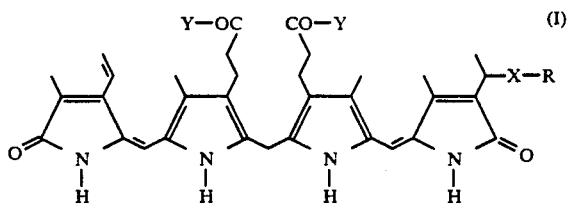

wherein

X stands for oxygen or sulfur

R stands for a $C_1$–$C_6$-alkyl group which is mono-or poly-substituted with carboxy, alkoxycarbonyl, hydroxy, mercapto, amino, alkyamino, dialkylamino or alkylcarbonyl amino groups and Y stands for amino, alkylamino, dialkylamino, hydroxy, alkoxy groups or the alkali salts thereof.

The use of bilirubin thioglycolic acid ether is preferred.

In addition to the analyte parameters, the liquid control and/or calibration serum in accordance with the invention can also contain additives, such as additional analyte stabilizers, detergents and preservatives, for example. If such additives are added, they must not interfere with the determination of other parameters. When ascorbic acid is added in preferred concentrations of 0.5 to 1.5 mg/dl, particularly preferred is a concentration of 0.9 mg/dl, the stability of the bilirubin derivatives will be further increased. A particularly high stability of the bilirubin derivative is achieved when the reagent is stored under an atmosphere of protective gas, particularly a protective atmosphere of $N_2$, combined with the addition of ascorbic acid. This atmosphere of protective gas does not only have advantageous effects on the stability of the bilirubin derivative but also on the stability of other parameters, e.g. uric acid. Stability of the bicarbonate value is achieved by adding appr. 0.3 vol.-% $CO_2$ to the $N_2$ inert gas. In addition to these analyte stabilizers, it is also possible to add other individual analyte-stabilizing additives. The addition of EDTA, for example, has a stabilizing effect on iron. The addition of a diluted Fe(II)-solution during the preparation of the control and/or calibration serum in the presence of EDTA, the preferred ratio being 1:1.1 (Fe/EDTA), leads to stable Fe-complexes that cannot be destroyed by lipoproteins and/or bovine serum albumin.

The addition of creatine has a positive effect on the stability of the parameter creatinine since creatinine hydrolysis is either prevented or at least greatly reduced.

In currently used control and/or calibration sera, an egg yolk fraction is used for the triglyceride parameter. However, turbidity cannot be excluded in such compositions. When glycerol is used as a triglyceride instead of the egg yolk fraction, this potential source of disturbance is positively excluded. Even when stored over a longer period of time, glycerol does not tend to cause turbidity and is, hence, extremely well suited for the use in the control and/or calibration serum of the invention.

Basically, all known preservatives can be used as such in the invention. The measurement of the parameters must, however, not be negatively affected. A combination of fungicidal and bactericidal preservatives has proven to be advantageous for the preservation of the liquid control and/or calibration serum of the invention. Particularly preferred is the use of gentamycin in a concentration of 100–150 µg/ml combined with 2,4-dichlorobenzyl alcohol in a concentration of 150–250 mg/dl. The use of a protective gas further supports the preservation.

Using a buffer, the pH value of the liquid control and/or calibration serum is set to be weakly alkaline. This preferred pH range is 8.2 to 8.6. The use of 20–100 mM TAPS (N-[tris(hydroxymethyl)methyl]-3-aminopropane sulfonic acid) buffer, particularly 50 mM, pH 8.3 has proven to be favorable. The weakly alkaline pH value has a positive effect on the stability of the control and/or calibration serum since it inhibits the growth of fungi. The concentration of the fungicide, if such an additive is required, can thus be kept at a low level and interferences with the parameter determinations can be excluded.

The preferred basis for a control and/or calibration serum in accordance with the invention is a serum albumin solution. In particularly preferred cases, a bovine serum albumin solution is used instead of the presently used human serum. The advantage of the bovine serum albumin solution is the lack of infectivity, especially with respect to infections with hepatitis and HIV viruses. Further, the use of a bovine serum albumin solution in comparison to human serum allows an exactly defined and reproducible basic formulation where deviations within a lot are considerably reduced. The desired parameter concentration is set in this basic matrix in the usual manner.

The basis for the preparation may also be a dry mixture which contains the desired analyte parameters including the bilirubin derivative of the formula (I). This mixture is dissolved in water until the desired concentration of the analyte parameter is obtained.

When kept in a closed container, the control and/or calibration serum of the invention is at 4° C. stable for more than 12 months. When stored at −20° C., stability can even be significantly increased. Even after the container is opened, the product is stable over a period of several days. It is excellently suited as a quality assurance and calibration serum for parameters used in clinical diagnostics, including especially bilirubin. The liquid control and/or calibration serum of the invention is particularly preferred in automated clinical diagnostics.

The following examples explain the invention in greater detail

EXAMPLE 1

Synthesis of Bilirubin Thioglycolic Acid Ether

An oxygen-free solution of 10 g bilirubin and 156 g thioglycolic acid in 6 liter dimethylformamide and 30 ml triethylamine are for 20 hours exposed to the light of a mercury lamp, the wavelength being >300 nm. The temperature of the solution should range between 30° and 60° C. The reaction can be monitored via thin layer chromatography (TLC: silica gel 60, eluting agent toluene/methanol/acetic acid=87/9/4). When the reaction is completed, dimethylformamide and triethylamine are removed in a high vacuum and the product precipitates from the thioglycolic acid which boils at a higher temperature. The product is then removed via filtration. Appr. 150 ml water are added to the remaining solution to precipitate any remaining product. The filtrates are combined and any remaining traces of the thioglycolic acid are washed out using 500 ml water and then 200 ml cold methanol. After drying in a high vacuum at 30° C., 8 g of a red product are obtained.

Thin Layer Chromatography: silica gel 60, eluting agent toluene/methanol/acetic acid=87/9/4)

Retention Factor=0.3

Mass Spectrum (negative FAB): m/e=675 (M-H)

EXAMPLE 2

Preparation of the Liquid Control and/or Calibration Serum for Use in Clinical Diagnostics 60 l water are mixed with 3.718 g EDTA sodium salt, 1.194 g $FeSO_4 \times 7\ H_2O$, appr. 10 l lipoprotein fraction, 241 ml gentamycin sulfate solution, 200 g Myacide ® SP (2,4-dichlorobenzyl alcohol) and 6 kg bovine serum albumin to produce a 100 l batch. This initial batch is stirred overnight at 4° causing the bovine serum albumine and Myacide ® SP to go in solution. On the second day, the following substance which have been dissolved before are added:

37.28 g KCl dissolved in 200 ml $H_2O$
44.11 g $CaCl_2 \times 2\ H_2O$ dissolved in 100 ml $H_2O$
30.50 g $MgCl_2 \times 6\ H_2O$ dissolved in 100 ml $H_2O$
22.65 g Na-L-lactate dissolved in 100 ml $H_2O$
26.73 g $NaH_2PO_4 \times H_2O$ dissolved in 100 ml $H_2O$
198 g glucose $\times H_2O$ dissolved in 1 l $H_2O$
130 g urea dissolved in 1 l $H_2O$
2.2 g creatinine dissolved in 100 ml $H_2O$
7.7 g creatine $\times H_2O$ dissolved in 100 ml $H_2O$
appr. 22 g glycerol dissolved in 100 ml $H_2O$
7.0 g $Li_2CO_3$ + 7.0 g uric acid dissolved in 1 l $H_2O$
1217 g TAPS dissolved in 2.5 l $H_2O$
881 mg ascorbic acid dissolved in 100 ml $H_2O$
318 g $Na_2CO_3$ dissolved in 3 l $H_2O$
6.6 g bilirubin thioglycolic acid ester dissolved in $Na_2CO_3$-solution
200–400 g NaCl (target value 135 mM $Na^+$) dissolved in 2.0 l $H_2O$
appr. 120 g tetramethylammonium chloride (target value 95 mM $Cl^-$) dissolved in 1.0 l $H_2O$
400–500 ml 2N acetic acid (or 2N NaOH) target value pH=8.3
$H_2O$ ad 100 l The liquid control and/or calibration serum is then filtered and sterilized and filled into suitable containers. The serum is overnight exposed to nitrogen gas and the containers are then closed.

The so-obtained liquid control and/or calibration serum contains the following components in the concentrations listed in Table 2.

TABLE 2

Analyte concentrations in the liquid control and/or calibration serum

| Analyte | Concentration |
| --- | --- |
| bilirubin | 4.8 mg/dl |
| cholesterol | 150 mg/dl |
| creatinine | 2.2 mg/dl |
| iron | 240 µg/dl |
| glucose | 180 mg/dl |
| uric acid | 7.0 mg/dl |
| urea | 130 mg/dl |
| lactate | 18 mg/dl |
| triglycerides | 180 mg/dl |
| phospholipids | 195 mg/dl |
| total protein | 6.0 g/dl |
| albumin | 6.0 g/dl |
| calcium | 3.0 mmol/l |
| phosphate | 6.0 mg/dl |
| magnesium | 1.5 mmol/l |
| sodium | 135 mmol/l |
| potassium | 5.0 mmol/l |
| chloride | 95 mmol/l |

We claim:

1. Liquid composition useful as a control serum or a calibration serum, comprising:

(a) a serum sample containing a known concentration of at least one analyte, and (b) a liquid stable bilirubin derivative of formula:

$$\text{(I)}$$

wherein

X stands for oxygen or sulfur

R stands for a $C_1$-$C_6$ alkyl group which is mono- or polysubstituted with carboxy, alkoxy carbonyl, hydroxy, mercapto, amino, alkylamino, dialkylamino or alkylcarbonylamino and Y stands for amino, alkylamino, dialkylamino, hydroxy, alkoxy groups, or the alkali salts thereof wherein said composition does not contain bilirubin.

2. The liquid composition of claim 1, wherein said bilirubin derivative is bilirubin thioglycolic acid ether.

3. The liquid composition of claim 1, further comprising a preservative.

4. The liquid composition of claim 3, wherein said preservative is a bactericide.

5. The liquid composition of claim 4, wherein said bactericide is gentamycin.

6. The liquid composition of claim 3, wherein said preservative is a fungicide.

7. The liquid composition of claim 6, wherein said fungicide is 2,4-dichlorobenzyl alcohol.

8. The liquid composition of claim 1, further comprising a stabilizer.

9. The liquid composition of claim 8, wherein said stabilizer is ascorbic acid.

10. The liquid composition of claim 9, wherein said ascorbic acid is present at a concentration of from 0.5 to 1.5 mg/dl.

11. Reagent useful as a control serum or a calibration system comprising the liquid composition of claim 1 stored under a protective gas.

12. Reagent composition of claim 11, wherein said protective gas is $N_2$.

13. Reagent composition of claim 11, wherein said protective gas comprises a mixture of $N_2$ and $CO_2$.

14. The liquid composition of claim 1, having a pH of from 8.2 to 8.6.

15. The liquid composition of claim 1, further comprising creatine.

16. The liquid composition of claim 1, wherein said serum sample is bovine serum albumin.

17. The liquid composition of claim 1, further comprising EDTA.

18. The liquid composition of claim 1, further comprising a ferrous ion salt.

19. Process for improving storage stability of a control serum or calibration serum wherein said serum does not contain bilirubin, comprising adding to said control serum or calibration serum an amount of a compound of formula

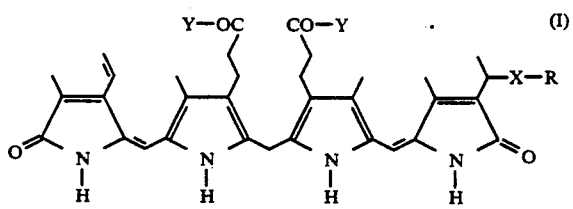

wherein
  X stands for oxygen or sulfur
  R stands for a $C_1$–$C_6$ alkyl group which is mono- or polysubstituted with carboxy, alkoxy carbonyl, hydroxy, mercapto, amino, alkylamino, dialkylamino or alkylcarbonylamino and
  Y stands for amino, alkylamino, dialkylamino, hydroxy, alkoxy groups, or the alkali salts thereof
in an amount sufficient to stabilize said control serum or calibration serum.